United States Patent [19]

Andersen et al.

[11] Patent Number: 5,371,671

[45] Date of Patent: Dec. 6, 1994

[54] DNA SEQUENCE AUTORADIOGRAM DIGITIZER AND METHODOLOGY IMPLEMENTED IN THE SAME

[75] Inventors: Robert D. Andersen, Santa Monica; Gregory C. Bristol, Los Angeles, both of Calif.

[73] Assignee: The Regents of the University of California, Oakland, Calif.

[21] Appl. No.: 111,031

[22] Filed: Aug. 24, 1993

Related U.S. Application Data

[63] Continuation of Ser. No. 492,818, Mar. 13, 1990, abandoned.

[51] Int. Cl.⁵ .............................................. G06F 15/00
[52] U.S. Cl. ................................................ 364/413.01
[58] Field of Search ........................ 364/413.01; 382/6; 435/6; 340/706, 711; 356/73, 389

[56] References Cited

U.S. PATENT DOCUMENTS

| | | | |
|---|---|---|---|
| 4,706,192 | 11/1987 | Nasu et al. | 364/413.01 |
| 4,837,687 | 6/1989 | Tanaka et al. | 364/413.01 |
| 4,885,696 | 12/1989 | Hara | 364/413.01 |
| 4,970,672 | 11/1990 | Snodgrass | 364/709.12 |
| 4,982,326 | 1/1991 | Kaneko | 364/413.01 |
| 5,121,320 | 6/1992 | Aoki et al. | 364/413.01 |

*Primary Examiner*—Roy N. Envall, Jr.
*Assistant Examiner*—Xuong M. Chung-Trans
*Attorney, Agent, or Firm*—Daniel L. Dawes

[57] ABSTRACT

An inexpensive manual reader for transcription of DNA sequence information from autoradiograms in computer data files is comprised of a gel code reader, electronic interface in software driven computer which provides full input and screening capability as well as storage and retrieval of DNA sequence data in predetermined DNA data base formats. The gel code reader comprises a linear optical magnifier and a thumb activated encoder. The electronic interface converts the data entered through the gel code reader into a plurality of computer compatible formats. The software driven computer then provides interactive voice synthesized editing and DNA data base storage.

7 Claims, 7 Drawing Sheets

110 →
- TO CHECK SEQUENCE DATA:

BASES ON SEQUENCING GEL → KEY-CURSOR PLUS INTERFACE → SEQUENCE DISPLAYED ON SCREEN → COMPARE TWO SEQUENCES, BASE BY BASE → IF MISS MATCH, GIVE WARNING TONE AND ERROR MESSAGE.

→ VOICE SYNTHESIZER → SPOKEN BASES AS FEEDBACK

112 →
- TO FIND A SEQUENCE IN DATA:

```
  BASES ON SEQUENCING GEL → KEY-CURSOR PLUS INTERFACE
              OR
  PRINTED BASE DATA → COMPUTER KEYBOARD
  ```

→ SEARCH FUNCTION: AS BASES ENTERED, SEARCHES AHEAD FOR COMPLETE SERIES. → SEQUENCE DISPLAYED ON SCREEN

→ TONES TO INDICATE PROGRESS OF SEARCH:
  LOW: STILL JUMPING AHEAD.
  HIGH: PRESENT LOCATION IS GOOD.
  VERY LOW: DEAD END.

→ HIGHLIGHT FOUND SERIES.

DNA SEQUENCE AUTORADIOGRAM DIGITIZER AND METHODOLOGY IMPLEMENTED IN THE SAME

This invention was made with Government support under Grant/Contract No. AM31183A awarded by the Department of Health and Human Resources, and Contract No. DE-FC03-87-ER60615.

This is a continuation of co-pending application Ser. No. 07/492,818 filed on Mar. 13, 1990, now abandoned.

BACKGROUND OF THE INVENTION

1. Field of the Invention

The field of the invention relates to apparatus and methodologies for the transcription of DNA sequence information from autoradiograms into computer data files.

2. Description of the Prior Art

The sequencing of DNA is an essential and often a routine tool in research laboratories in biological and medical sciences. DNA sequence analysis allows identification of the genes, which are the building blocks of hereditary material. DNA sequencing makes possible many powerful new clinical diagnostic techniques. Technologies utilizing DNA sequence information have revolutionized forensic medicine, fetal and neonatal diagnosis, and basic research into the nature of genetic expression.

The need and use for DNA sequencing has created, in turn, a need for an effective device to read DNA sequence information and to store this information into computer file for subsequent analysis. Heretofore, the prior art has devised three types of devices which address this need.

First, automated DNA sequencers have been made which use either fluorescent labeled or radiolabeled DNA probes in combination with light or particle detection devices.

Second, autoradiogram or film digitizers have been developed and rely on charge coupled devices and pattern recognition software to encode and analyze the film data.

Third, sonic location devices have been provided which allow a manual sequencing of autoradiograms.

In each of these prior art approaches the end result is a computer file containing a DNA sequence. This sequence readout typically consists of alphabetic characters A,C,G,T which are abbreviations for the nucleotides adenine, cytosine, guanine and thymine respectively. Typical prior art automated DNA sequencers and autoradiogram digitizers are expensive, costing between $50,000-100,000 in 1990 dollars. In addition, the results produced by those sequencers and digitizers require extensive software analysis. The use of sonic location devices is less expensive, costing approximately 2,500 dollars in present value. However, the limitations of such sonic readers is the reliance on a pointer which must be tapped within a given length, i.e. A,C,G,or T in succession to identify the nucleotide being read. Because gel compression makes it increasingly difficult to identify the next nucleotide band, this necessitates using both a magnifier and a fine cursor line for accurate reading. Both these limitations of a sonic device impede the use of a pointer tapped on a sequence band.

Therefore, what is needed is an apparatus and methodology which is inexpensive yet overcomes the limitations of the less expensive DNA sequencing devices known in the prior art.

BRIEF SUMMARY OF THE INVENTION

The invention is a DNA sequence autoradiogram digitizer comprising a gel code reader manually manipulatable over the autoradiogram for optically magnifying the autoradiogram and providing an element for manually inputting data relating to the autoradiogram. An interface element is coupled to the gel code reader for providing computer compatible data output derived from the data manually input through the gel code reader. A programmed computer is coupled to the interface element for processing data derived from the manually input data input through the gel code reader.

As a result, DNA sequence data can be inexpensively input from the autoradiogram at a high rate.

The gel code reader comprises a lens for magnifying a selected portion of the autoradiogram and an input element for allowing manual input of data relating to the selected portion of the autoradiogram. The lens element comprises a half cylinder lens. The half cylinder lens is comprised of a half cylindrical surface and an adjoining flat surface. The flat surface has disposed thereon a cursor line for registration of the gel code reader relative to the autoradiogram.

The input element comprises a plurality of momentary contact switches. Each switch is user definable through the computer to signify presence of one nucleotide selected from the group including adenine, cytosine, guanine, and thymine.

The computer comprises an editing element for editing the data received by the computer from the gel code reader through the interface element.

The computer element is a data base element for configuring the data received from the gel code reader through the interface element into a predetermined data base format. Mass memory storage is provided for storing large amounts of data and a transfer element for transferring the formatted data base data into the mass storage element.

The computer comprises a voice synthesizer element for producing audio voice messages corresponding to the data received from the gel code reader through the interface element. The computer comprises an editing element for editing the data received by the computer from the gel code reader through the interface element and a talk-back element for producing an audio feedback corresponding to a selected character of displayed data received by the computer so that the data received by the computer is read back as it is edited.

The invention and its various embodiments can better be visualized by now turning to the following drawings wherein like elements are referenced by like numerals and wherein a series of elements are represented by alphanumeric reference numerals, e.g. 20a-d, representing 20a, 20b, 20c and 20d.

The invention and its various embodiments can be better understood by now turning to the following detailed description.

DETAILED DESCRIPTION OF THE PREFERRED EMBODIMENTS

The invention is an inexpensive reader for transcription of DNA sequence information from autoradiograms into computer data files. As shown in the simplified diagram of FIG. 5, the system is comprised of a gel reader 10 coupled to a computer interface unit 12 which in turn is coupled to a computer 14. Gel reader 10 is utilized to read the DNA sequence bands 16 imprinted on a film 18. As will be described in greater detail in connection with FIGS. 1 and 2, gel reader 10 is comprised of a magnifier and thumb activated encoder. Software, described below, provides input control at full screen editing capabilities as well as storage retrieval of DNA sequence data.

Figure 1:
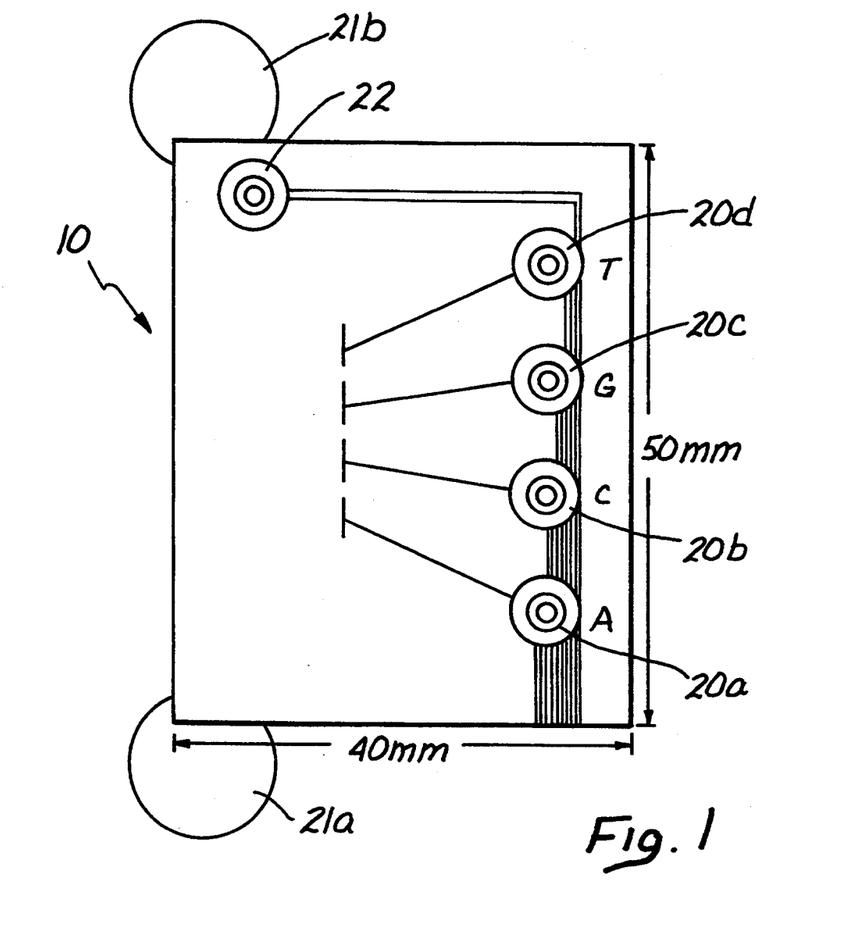
FIG. 1 is a top planned view of the gel reader devised according to the invention.
Figure 2:
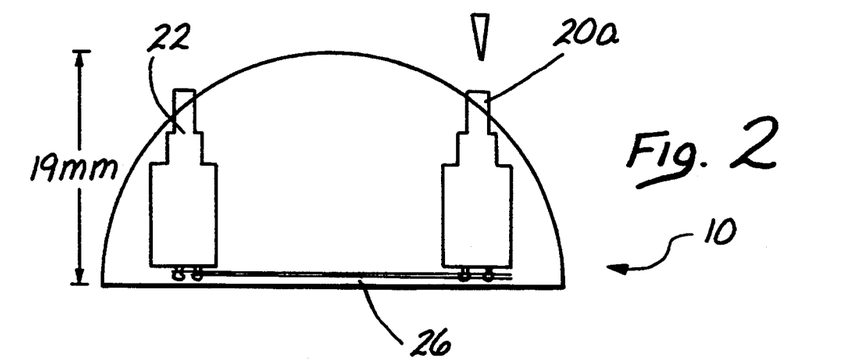
FIG. 2 is a side view of the gel reader shown in FIG. 1.

Turn now to the depictions of FIGS. 1 and 2 wherein gel reader 10 is shown in top plan view in FIG. 1 and in side cross-sectional view in FIG. 2. Gel reader 10 is formed from a half cylinder of transparent Plexiglass or other optical material to provide both magnification and angled viewing of the DNA sequence ladder when film 18 is read. Four electric pushbutton switches 20a–20d are exposed in corresponding bores defined along one longitudinal line within the body of gel reader 10 and can be manually activated by the user to denote which of the nucleotides are read from one band within the DNA sequence on film 18. Any switches now known or later devised may be employed such as pressure sensitive switches, heat sensitive switches or the like. As described below switches 20a–d may be user programmed to represent the nucleotides in any order, or for that matter arbitrarily user defined to signify any variable desired.

An identical fifth pushbutton switch 22 is disposed in a mating bore also defined within gel reader 10 shown in the illustrated embodiment shown in the top right hand corner when viewed from the line formed by switches 20a–20d. Switch 22 is used as a delete key or may be user programmable for another character entry. Gel reader keys are also used for purposes other than character entry as described below, namely as function or control keys.

In practice, the four sequence buttons 20a–20d are depressed by the left and right thumbs as gel reader 10 is held on its left and right side by the coders left and right hands. Finger pads 21a and b are provided for comfort and ease of manual manipulation of reader 10. Use of the thumbs is utilized in the preferred embodiment, because of the greater strength in thumbs as opposed to the other fingers on the hand thus allowing longer use before tiring.

A cursor line 24 is defined on the bottom surface 26 of gel reader 10 to allow registration of adjacent DNA sequence bands in accurate sequential input. Cursor 24 may be permanently defined into base surface 26 or attached by a transferred template. In the preferred embodiment cursor line 24 is attached to base surface 26 through magnetic attachment of a transparent template sheet through the use of thin strip magnets (not shown). Other means of mechanical attachment are easily substituted for this purpose.

A sequence autoradiogram is placed on a conventional light box 28 diagrammatically depicted in FIG. 1 and gel reader 10 is positioned over the sequenced lengths to be transcribed. A practiced encoder can then input data at about one nucleotide per second or between 2,000 to 3,000 nucleotides per hour.

Figure 3:
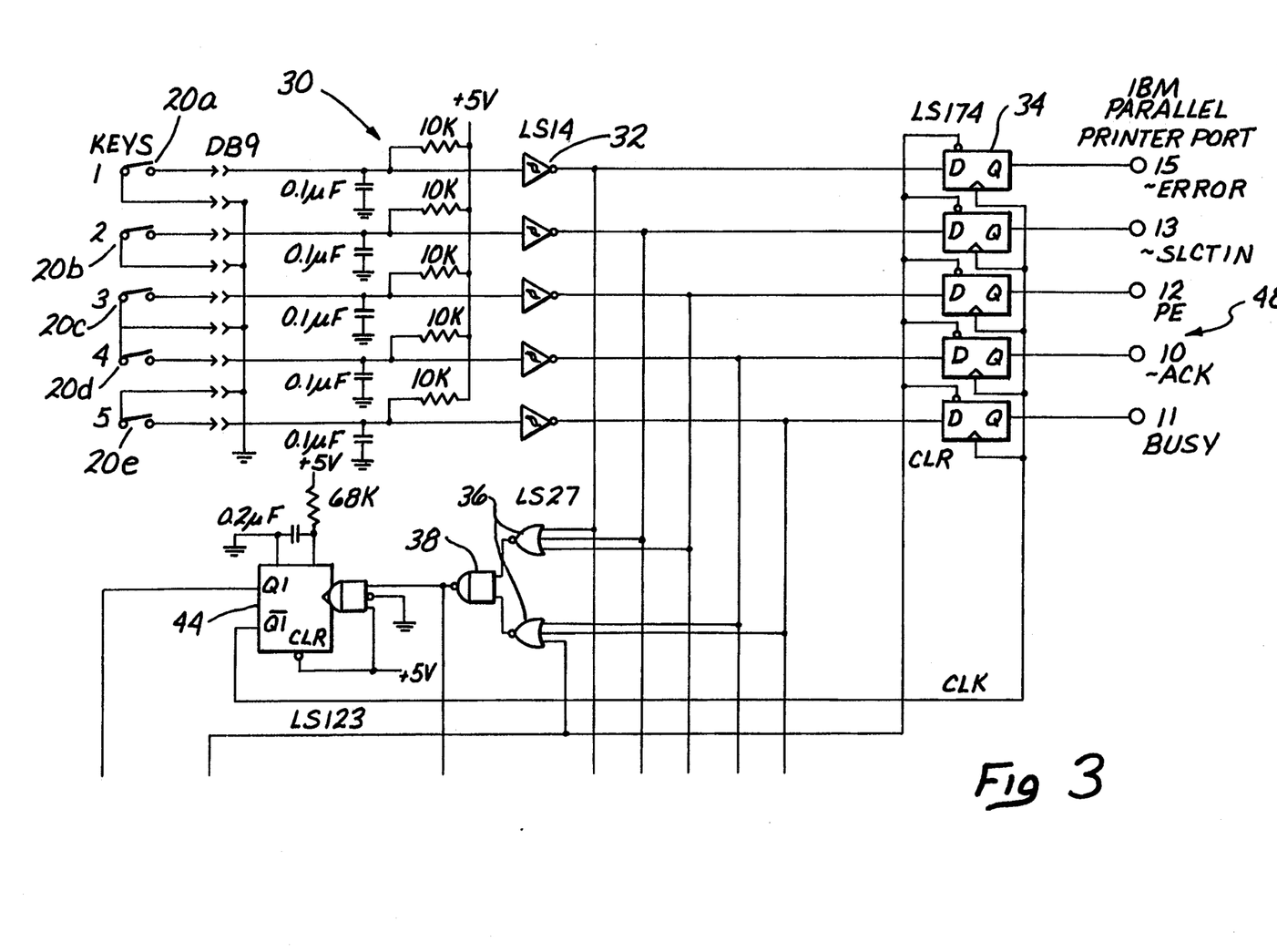
FIG. 3 is a schematic diagram of the computer interface unit which is coupled between the gel reader of FIGS. 1 and 2 and personal computer which receives the input information

Turn now to FIG. 3 wherein a schematic diagram of interface unit 12 is shown. The five keys 20a–d and 22 are coupled through RC debounce circuits, generally denoted by reference numeral 30. The output of the debounce circuits 30 is coupled in each case to a Schmidt trigger 32 which produces a high output when its corresponding button 20a–20d or 22 is momentarily depressed. The output of Schmidt triggers 32 are coupled to corresponding latches 34. The output of latches 34 are coupled to the status lines of a parallel printer port of standard IBM format as depicted in FIG. 3. Normally the IBM parallel printer port of a personal computer is considered an output port only. However, the status lines of that port allow bidirectional communication and can be read by appropriate software. This allows input in parallel format without alteration of the personal computer's conventional port structure.

The output of Schmidt triggers 32 are also coupled in parallel to the inputs of nor-gates 36 whose output, in turn, is coupled to nand-gate 38. The output of nand-gate 38, in turn, is provided as one input to and-gate 40. The output of and-gate 40 is coupled to the clock input of flip flop 42. The output, Q2 of flip flop 42 in turn is coupled to the clear reset terminals of latches 34. The time delay through the circuitry beginning with gates 36 through the clear reset of input 34 is approximately 20 milliseconds. However, latches 34 are strobed by a shorter pulse, CLK, coupled to the clock inputs of latches 34 and derived from the ~Q output of flip flop 44. Flip flop 44 in turn is clocked by the output derived from nand-gate 38 coupled to and-gate 46 which is in turn is coupled to the clock input of flip flop 44. The ~Q1 output of flip flop output 41 goes active approximately 50 milliseconds earlier than the Q2 output of flip flop 42, thereby strobing the input of switches 20a–d and 22 prior to resetting latches 34.

During this 50 millisecond period, computer 14, which may be a conventional IBM personal computer reads the parallel port 48 and following any change of state which occurs. In the case of DNA sequencing, only one nucleotide per line is input, so that each depression of a switch 20a–d is a separate data input.

Meanwhile the output of Schmidt triggers 32 are also provided to a buffer and parallel-to-serial converter 50. The baud rate of the serial communication is provided by baud rate generator 64 which is crystal controlled. Converter 50 converts the data from keys 20a–d and 22 into a predetermined serial communications protocol, which in the illustrated embodiment is chosen at 1200 baud, 8 data bits, 2 stop bits, and no parity. Converter 50 is reset on power up with a 5 millisecond signal generated by Schmidt trigger 52. Converter 50 is triggered by the Q1 output from flip flop 44 which is stored within latch 54. The output of latch 54 in turn is coupled to the data strobe input of converter 50. The input of the signal from Q1 to flip flop 44 into one shot multivibrator 54 triggers a 10 microsecond pulse to data strobe input of converter 50 thereby activating serial data transmission.

The serial output of converter 50 is coupled into a serial driver 58. Serial driver 58 in the illustrated embodiment is an RS232 driver device which provides the output for both an IBM format serial port 60 and a Macintoch serial port 62. Power is provided by a conventional power supply 66.

Figure 5:
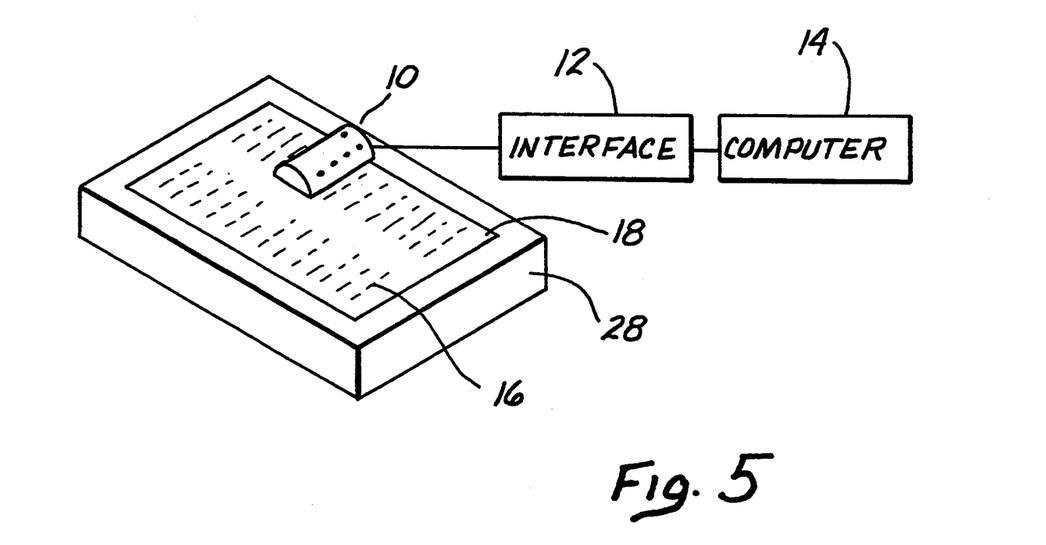
FIG. 5 is a block diagram of the assembled system comprised of the gel reader, computer interface and computer unit.

Considering now the methodology of the invention and its implementation within the system of FIG. 5 and in particular within computer 14. In the illustrated embodiment the computer program, named Usedit, (pronounced "you said it") is written in the Microsoft Quick Basic 4.5 and is attached as an appendix.

Parallel port 48 and serial port 60 and 62 are each polled to determine if there has been any change of state on any one of the lines due to a button press. Null signals from the serial line are ignored and only changes from the parallel port status bits are decoded. Arbitrary assignment to the DNA basis to buttons 20a–20d other than that depicted for the sake of illustration in FIG. 1 is permitted. In other words, instead of the sequence of A,C,G,T corresponding to buttons 20a–d respectively any other sequences the user may define can be employed. In addition, user defined protocol for audio outputs in response to a button depression is provided, such as either tones, or a synthesized voice announcing the nucleotide entered or silence can be provided by computer 14 as may be desired. These user selected configurations are stored within the program in a configuration file, entitled USEDIT.CFG. Voice mnemonics are configured in a file, USEDIT.SPK.

After the sequence input is completed, the data may be stored in an output disk file included as part of computer 14 or driven as peripheral to computer 14 in a conventional manner. Any one of a number of presently known DNA data base formats can be used such a Staden, University of Wisconsin, GenBank or EMBL.

The program provides extensive editing capabilities. Full screen editing may be done at any time during entry of a new sequence data or editing of preexisting data. Once entered in the data file a voice synthesized talk back of sequence information is generated in a proofreading mode to allow control over error detection and correction. During editing and proofreading gel reader 10 can be utilized as a mouse to perform various processing functions such as on/off function through delete button 22 or talk back graduated speed buttons through the use of buttons 22a–22d.

A FIND MODE allows a searcher to locate a user defined sequence within the RNA sequence data. Use of the find mode is especially beneficial to refind a place in the sequence as a result of interruption of the data entry. A CHECK MODE allows the user to reread an autoradiogram and check it against an archive file.

Specific nucleotides can be located in the file with a FIND MODE and tagged or highlighted. The found feature can then be compared with the sequence of the gel using a check mode. In the check mode, the processing program indicates by tone or voice whether there is a disagreement between the data entry in the data file. A screen prompt is generated for correction of the data file if needed. When data is written to a disk, the program, USEDIT prompts for file name. If editing an existing file, that file can be overwritten or stored as a new file. In the illustrated embodiment the program stores sequence data in a conventional Staden format which is comprised of 60 nucleotides per line. The program generates an ASCII data file which is compatible with conventional pattern programs as well as other DNA sequence handling programs to allow for DNA sequence data base assembly and analysis.

In the talk back mode, computer 14 uses the voice synthesis capabilities of the program with an HV 2000 computer voice card from Zenith Data Systems. The program could be modified by those with ordinary skill art to utilize other voice synthesizing cards or simply use a tone feedback without voice synthesization. The mode in which USEDIT program runs is user determined through USEDIT. CFG file or alternatively by an assumed default condition. Port assignment, button order, and tone and voice modes are stored in the configuration file.

Figure 4A:
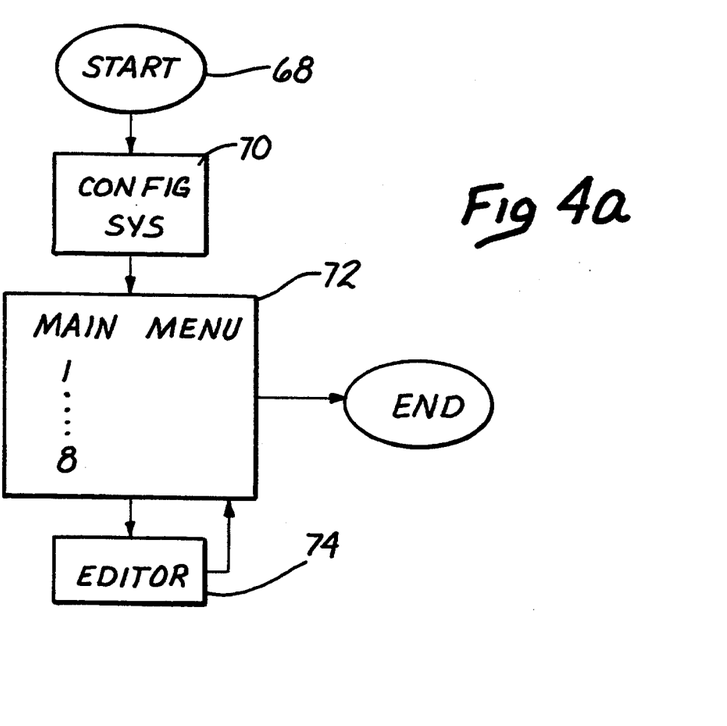
FIG. 4a is a diagrammatic flow chart of the main menu portion of the methodology of the invention as implemented in the system depicted in FIG. 5.

The operation of the apparatus as shown in FIG. 4a begins at step 68. The system is configured at step 70 wherein port configurations and drivers are determined. For example, if a voice synthesizer is to be used, the location of the voice driver is determined and if there is none, then vocalization is disabled in the computer by the setting of a flag. The program looks for USEDIT.SPK, the file containing pronunciation parameters for the HV2000 voice synthesizer. If not found, a default set of parameters is used. The input port is searched for in USEDIT. CFG. If the port is not found, then a utility program or message to utilize a utility program is called or prompted in order to allow the user to manually enter which port, serial or parallel, will be utilized in the program. Various video parameters are set, such as color or black and white displays; the button significance or order is set on gel code reader 10; and the feedback sound which the user desires when a button is pressed, such as tones, talkback or silence, is selected.

Thereafter, the methodology enters a main menu screen at step 72 wherein eight options are user-selectable. In the illustrated embodiment, the first option on the main menu 72 is an EDIT SEQUENCE, which if selected, opens or calls an editor program depicted in FIG. 4b and then presents the user with a blank input screen according to the selected data format.

Figure 4B:
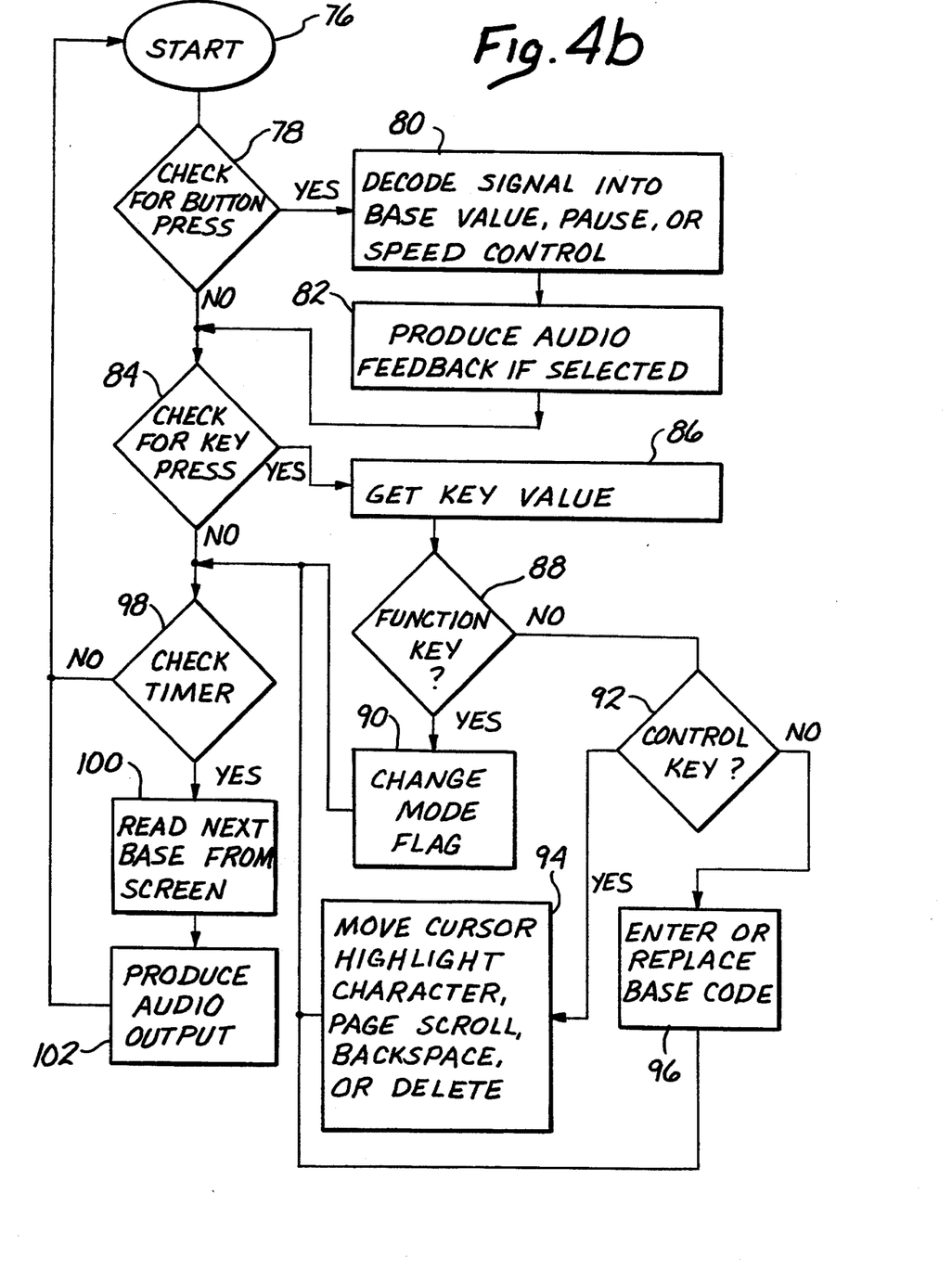
FIG. 4b is a diagrammatic flow chart of the editor portion of the methodology of the invention as implemented in the system depicted in FIG. 5.

A second option on main menu step 72 is an EDIT OLD SEQUENCE option which if selected requests a user-selected file and, if available, reads it and then calls the editor program of FIG. 4b with a display of the DNA sequence file thus read.

The third option within main menu step 72 is a SAVE SEQUENCE option. If the SAVE SEQUENCE option is selected, the file is saved under a user-selected name, or if the user has not selected a name is saved under a default name to a disk or other mass storage device.

The fourth option or main menu step 72 is SAVE UNDER NEW NAME option and requests a new user-selected name to save the data held in memory to disk or another miss storage device.

The fifth option under main menu step 72 is a RE-EDIT SEQUENCE option. If RE-EDIT SEQUENCE is selected, the sequence, which is held in memory, if any, is displayed in the editor module which is called to allow editing as described below.

In addition to the first five options which call up the editor subprogram, there are three additional options in the presently illustrated embodiment of main menu step 72. For example, the sixth option is a change button order option which requests a new button order for gel code reader 10, sets it and then automatically changes the configuration of the file which will be called up at step 70 during start-up of the program.

A seventh option is to change the reader port. If the CHANGE READER PORT option is selected, a new user-selected reader port is requested, it is set, and then the configuration file is changed appropriately so that it responds when step 70 is entered.

The final option available in the presently illustrated embodiment of main menu 72 is a CYCLE-SOUND option. CYCLE-SOUND cycles among the various feedback sounds which are permitted when a keyboard stroke is entered or a button pushed in gel reader 10 is made. In the illustrated embodiment, these sounds cycle between silence, tone, or a synthesized voice talkback or a character which is highlighted. In the illustrated embodiment, only characters can be highlighted in the editor program and thus read back.

Turn now to FIG. 4b where the editor program 74 is illustrated. The methodology begins with step 76 and then enters a main loop comprised of three steps. First, a check is made at step 78 to determined whether or not a button on gel code reader 10 has been pressed. If it has, the button is decoded into a base nucleotide corresponding to one of the nucleotide bases which have been predefined or another user-defined symbol, or if the editor has been placed in a different mode, as described below, such as the TALK-BACK MODE, a button press on gel code reader 10 can vary the speed of the audio or voice synthesized talk back, or create a pause, as implemented at step 80. If editor 74 is not in a TALK-BACK MODE, then an audio feedback signal is produced at step 82. For example, if button 20a is pressed the voice synthesizer within the computer will audibly say the letter "A", thereby providing an intelligible feedback signal to the operator who otherwise has all of his or her attention directed to the manipulation of gel code reader 10 and the reading of the autoradiogram.

If a button on gel code reader 10 has not been pressed, then editor 74 in the main loop checks at step 84 to determine whether or not a key has been pressed on the keyboard. If it has, the value of the key pressed is obtained at step 86. A keyboard press, however, may not necessarily be an alphanumeric key, but may be a function or control key as well. For example, main loop checks at step 88 determine if a function key is pressed. If the function key has been pressed, as determined at step 88, this causes a mode flag to be changed at step 90 with return to the next step of the main loop which starts at step 70. If the function key has not been pressed, then the main loop determines at step 92 whether or not a control key has been pressed. If a control key has been pressed this is then variously interpreted as either a cursor movement, a highlighting of a character where the cursor stands, a page scroll, back space or deletion of the character as determined by the nature of the control key stroke as implemented in step 94. Control then returns to the next step of the loop. However, if the keyboard stroke is neither a function key or a control key, it is then assumed to be an alphanumeric key and its value is entered or it is used to replace the base code where the cursor sat at step 96 with return to the next step of the main loop.

If there is neither a button pressed on gel code reader 10, as determined at step 78, nor keyboard press at step 84, then a timeout signal from an internal timer within the computer is checked at step 98. If the timeout has not occurred, then processing returns to the beginning of main loop 76. However, if the timeout has occurred, then the next base is read from the screen at step 100 and an audio feedback signal produced at step 102. The timer is enabled, as described below, during the TALK-BACK MODE and is otherwise disabled during the normal EDIT MODE.

The program outlined in connection with FIGS. 4a and 4b above is capable of operating in a variety of modes wherein a different significance will be attributed to the key stroke depending on the mode. As described generally above, there are two edit modes which are similar to normal word processing modes wherein characters may be entered either through gel code reader 10 or a separate keyboard as an insert or as an overwrite. In the insert mode, a new character is placed in front of the highlighted character with the remaining characters shifted down one space. In the overwrite mode, a new character is placed in lieu of the character at which the cursor was positioned when the input was made.

In addition to the EDIT MODE there is a TALK-BACK MODE, CHECK MODE and FIND MODE as discussed generally above. In the TALK-BACK MODE, the user rereads the DNA sequence autoradiogram as the computer voice reads the input DNA sequence record in memory. The characters from the stored DNA sequence are read according to the timer speeds entered into the computer through gel code reader 10 at step 80 and as sequenced in the data sequence file by steps 98–102 in FIG. 4b. If the user sees that an incorrect nucleotide base has been entered he may then stop the program, enter the EDIT MODE, make the corrections and then reenter the TALK-BACK MODE from the point where he stopped.

In the CHECK MODE the user reenters the sequence with gel code reader a second time. Meanwhile, the computer simultaneously reads the data sequence stored in the data sequence file in synchronization with the second read input from the user. If the second input matches the first input, the preselect tone or voice signal provided by the computer as described above in connection with steps 78–82. However, if there is an error a distinguishable audio signal is produced and the user is then free to exit the CHECK MODE and make an edit entry in the EDIT MODE and then return to the CHECK MODE and continue reentering the data.

The FIND MODE allows the user to exit the system and then come back at a later time and quickly and conveniently find the DNA base sequence where he left off. Again this is performed through steps 78–82 of FIG. 4a but with a different mode flag set and therefore a different reaction being undertaken by the computer in response to the activations of the pushbutton switches of gel code reader 10.

For example, the user may have read the sequence ACCGGTT from the autoradiogram, saved the file and then left for some period of time. If upon returning the viewer may want to read the autoradiogram where he left off. This is accomplished by selecting the FIND MODE, sequentially pushing the buttons A-C-C-G-T-T. As each button on gel code reader 10 is pressed the cursor moves from the beginning of the data sequence file, for example, to the first occurrence where there is a nucleotide base A. Then after the C is pressed, it will move to the first occurrence of an AC. After the second C is pressed, it then moves and highlights the first occurrence of the sequence ACC and so forth until it finds the unique point in the DNA sequence where the exact series in order of nucleotide bases are to be found.

Figure 4C:
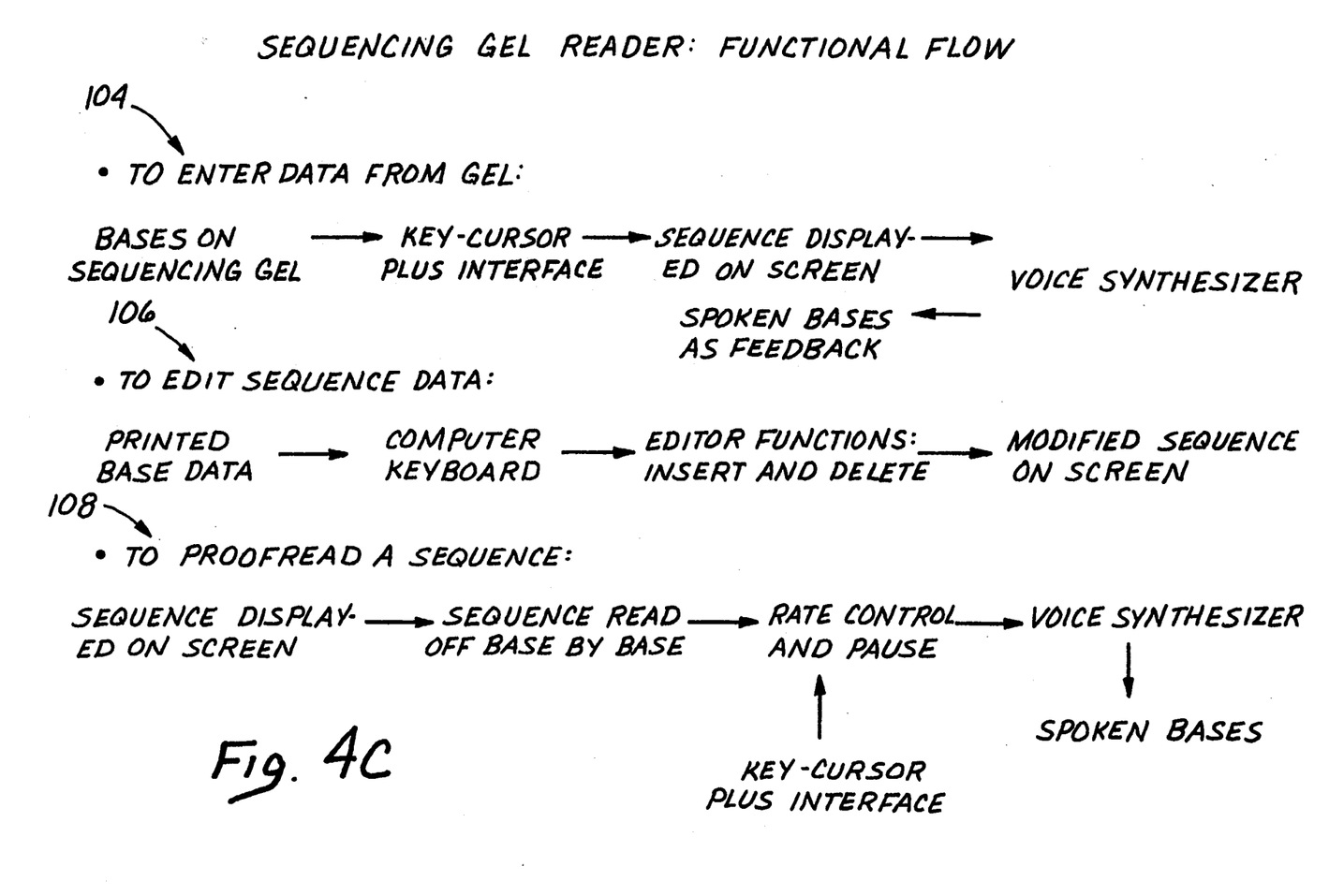
FIG. 4c is a diagrammatic chart of the modes of the methodology of the invention as implemented in the system depicted in FIG. 5.

Turn now to FIG. 4c wherein the various modes of operation of the program as depicted in FIGS. 4a and 4b are diagrammatically illustrated. To enter data from the autoradiogram gel, the bases on the sequencing gel are read with the key cursor through the interface so that the sequence is displayed on the screen. With each insert the synthesized voice feedback announces which base has been entered as depicted in the sequence series 104.

In the EDIT SEQUENCE series generally denoted by reference numeral 106, edit sequence is entered. A nucleotide base data file is printed on the screen and then manipulated through control functions on the computer keyboard to place the cursor at user selected positions in which deletions or insertions can be made in order to modify the sequence on the screen if desired.

In the PROOFREAD SEQUENCE generally denoted by reference numeral 108, the sequence to be proofread is displayed on the screen and the sequence is read off on a serial base-by-base basis by the voice synthesizer (TALK-BACK MODE). The rate of the synthesizer's read and any pause inserted is controlled by activation of gel code reader 10 through the interface. The rate having been determined, the voice synthesizer speaks the bases as the user reads them on the sequencing gel.

In the CHECK SEQUENCING mode referenced by reference numeral 110, the sequence to be checked is displayed on the screen and the user reads the bases on the sequencing gel by reinputting the data through the gel code reader 10 through the interface. The two sequences are then compared on a base-by-base series. If there is a mismatch a warning tone, an error message is given by the voice synthesizer.

Finally, the FIND SEQUENCE mode, generally denoted by reference numeral 112, is depicted at the bottom of FIG. 4c. To find where in the data sequence file a particular base sequence is located, the user displays the sequence data on the computer screen and then either seeks the particular sequence through the computer keyboard or inputs the sequence which he is searching for from a direct read from the sequencing gel of the autoradiogram through gel code reader 10 of the interface. As the bases are entered, a search is made forward through the sequence database on a cumulative basis with the nearest sequence combination satisfying the search being highlighted. Feedback tones are provided to indicate the progress of the search. A low tone is provided to indicate that the search is still jumping ahead and a high tone is indicated, for example, to show that the location has been found. If the entire database has been searched without a find, then a third very low tone is sounded to indicate a failure to find.

Many alterations and modifications may be made by those having any ordinary skill in the art without departing from the spirit of the scope of the invention. Therefore, it must be understood that the illustrated embodiment has been set forth only for the purposes of example and should not be taken as limiting the invention which is defined by the following claims which expressly include all means for performing the same function even though they may not perform the same function in substantially the same manner.

We claim:

1. A method for processing nucleotide base data in a DNA sequencing autoradiogram comprising the steps of:
   manually placing an optical gel code reader over said autoradiogram;
   manually activating at least one switch on said gel code reader in response to a selected nucleotide base in predetermined registration with said gel code reader;
   generating a data signal corresponding to said manually activated switch to input to a computer:
   entering a predetermined corresponding nucleotide base code corresponding to said selectively activated switch into a predetermined database format; and
   selecting a mode within said computer wherein activation of said gel code reader switches and of a keyboard are interpreted according to said mode selected.

2. The method of claim 1 where in said step of selecting said mode comprises the step of selecting an EDIT MODE wherein said nucleotide base entries within said computer is edited in a selected manner.

3. The method of claim 1 where in said step of selecting said mode said mode is a TALK-BACK MODE wherein said DNA sequence stored within said computer is automatically audibly read back through voice synthesis to permit visual checking of said autoradiogram in verification of said sequence of nucleotide bases entered in said computer.

4. The method of claim 1 where said step of selecting said mode selects a check sequence mode comprising the steps of repeating said steps of manually placing said gel code reader over said autoradiogram, repeating said step of manually activating said switches on said gel code reader, and generating a comparison signal in synchronization with entry of nucleotide bases entered through said gel code reader to indicate whether nucleotide bases stored within said computer, which are read in order and in synchronization with activations of said repeated step of activating said buttons of said gel code reader compare accurately or not.

5. A method for processing nucleotide base data in a DNA sequencing autoradiogram comprising the steps of:
   manually placing an optical gel code reader over said autoradiogram;
   manually activating at least one switch on said gel code reader in response to a selected nucleotide base in predetermined registration with said gel code reader;
   generating a data signal corresponding to said manually activated switch to input to a computer;
   entering a predetermined corresponding nucleotide base code corresponding to said selectively activated switch into a predetermined database format;
   providing a selected audio feedback in response to entry of said nucleotide base code into said computer; and
   selecting a mode within said computer wherein activation of said gel code reader switches and of a keyboard are interpreted according to said mode selected;
   where said step of selecting said mode selects a find sequence mode comprising:

the steps of serially entering a selected nucleotide base sequence to form a series of nucleotide bases;

advancing through said database of sequences of nucleotide bases stored within said computer to find a nucleotide base sequence which matches at least in part said series formed from said selected nucleotide base sequence;

repeating said steps of serially entering a selected nucleotide base sequence to form said series of nucleotide bases, and advancing through said database of sequences of nucleotide bases stored within said computer to find a nucleotide base sequence which matches, said series being concatenated with each additional entry of a selected nucleotide base until a complete sequence of nucleotide bases has been entered and a final matching sequence found within said nucleotide sequences database stored within said computer; and generating distinguishable audio tones within said computer at each entry of said nucleotide database to indicate searching for said sequence, finding said sequence and failing to find said sequence as is appropriate at each step.

6. A method for processing nucleotide base data in a DNA sequencing autoradiogram comprising the steps of:

manually placing an optical gel code reader over said autoradiogram;

manually activating at least one switch on said gel code reader in response to a selected nucleotide base in predetermined registration with said gel code reader;

generating a data signal corresponding to said manually activated switch to input to a computer;

entering a predetermined corresponding nucleotide base code corresponding to said selectively activated switch into a predetermined database format;

providing a selected audio feedback in response to entry of said nucleotide base code into said computer; and selecting a mode within said computer wherein activation of said gel code reader switches and of a keyboard are interpreted according to said mode selected;

where said step of selecting said mode selects: an EDIT MODE wherein said nucleotide base entries within said computer is edited in a selected manner, where said EDIT MODE is a TALK-BACK MODE wherein said DNA sequence stored within said computer is automatically audibly read back through voice synthesis to permit visual checking of said autoradiogram in verification of sequence of nucleotide bases entered in said computer;

a check sequence mode comprising the steps of repeating said steps of manually placing said gel code reader over said autoradiogram, repeating said step of manually activating said switches on said gel code reader, and generating a comparison signal in synchronization to entry of nucleotide bases entered through said gel code reader to indicate whether nucleotide bases stored within some computer read in order and in synchronization with activations of said repeated step of activating said buttons of said gel code reader compare accurately or not; and a find sequence mode comprising the steps of entering in series a selected nucleotide base sequence, advancing through said database of nucleotide bases stored within said computer to the nearest matching series, said series being cumulative expanded with each additional entry of a nucleotide base until said entire sequence of nucleotide bases has been entered and a matching sequence found within said nucleotide sequence database stored within said computer, audio tones being generated within said computer at each entry of said nucleotide database indicating searching for said sequence, finding said sequence and failing to find said sequence as is appropriate at each step.

7. A method for processing nucleotide base data in a DNA sequencing autoradiogram comprising the steps of:

manually placing an optical gel code reader over said autoradiogram;

manually activating at least one switch on said gel code reader in response to a selected nucleotide base in predetermined registration with said gel code reader;

generating a data signal corresponding to said manually activated switch to input to a computer; and entering a predetermined corresponding nucleotide base code corresponding to said selectively activated switch into a predetermined database format, where said step of selecting said mode selects an EDIT MODE wherein said nucleotide base entries within said computer is edited in a selected manner;

where in said step of selecting said mode said mode is a TALK-BACK MODE wherein said DNA sequence stored within said computer is automatically audibly read back through voice synthesis to permit visual checking of said autoradiogram in verification of said sequence of nucleotide bases entered in said computer;

where in said step of selecting said mode said mode is a check sequence mode comprising the steps of repeating said steps of manually placing said gel code reader over said autoradiogram, repeating said step of manually activating said switches on said gel code reader, and generating a comparison signal in synchronization to entry of nucleotide bases entered through said gel code reader to indicate whether nucleotide bases stored within some computer read in order and in synchronization with activations of said repeated step of activating said buttons of said gel code reader compare accurately or not; and where in said step of selecting said mode said mode is a find sequence mode comprising the steps of entering in series a selected nucleotide base sequence, advancing through said database of nucleotide bases stored within said computer to the nearest matching series, said series being cumulative expanded with each additional entry of a nucleotide base until said entire sequence of nucleotide bases has been entered and a matching sequence found within said nucleotide sequence database stored within said computer, audio tones being generated within said computer at each entry of said nucleotide database indicating searching for said sequence, finding said sequence and failing to find said sequence as is appropriate at each step.

* * * * *